United States Patent
Secrest et al.

(10) Patent No.: US 6,666,847 B2
(45) Date of Patent: Dec. 23, 2003

(54) DUODENOSCOPE NEEDLE

(75) Inventors: Dean J. Secrest, Concord, OH (US); Marlin E. Younker, West Palm Beach, FL (US); William Greuloch, Westlake, OH (US)

(73) Assignee: US Endoscopy Group, Inc., Mentor, OH (US)

( * ) Notice: Subject to any disclaimer, the term of this patent is extended or adjusted under 35 U.S.C. 154(b) by 0 days.

(21) Appl. No.: 10/146,525

(22) Filed: May 15, 2002

(65) Prior Publication Data

US 2002/0193741 A1 Dec. 19, 2002

Related U.S. Application Data

(60) Provisional application No. 60/292,169, filed on May 18, 2001.

(51) Int. Cl.[7] .............................................. A61M 5/178
(52) U.S. Cl. ............. 604/164.01; 604/265; 604/164.06; 604/164.09; 604/165.01
(58) Field of Search ........................ 604/164.01, 164.06, 604/265, 165.01, 164.09

(56) References Cited

U.S. PATENT DOCUMENTS

| | | | | |
|---|---|---|---|---|
| 4,578,061 A | * | 3/1986 | Lemelson | 604/170.01 |
| 4,950,257 A | * | 8/1990 | Hibbs et al. | 604/265 |
| 6,126,633 A | * | 10/2000 | Kaji et al. | 604/95.04 |
| 6,540,725 B1 | * | 4/2003 | Ponzi | 604/272 |
| 2002/0019623 A1 | * | 2/2002 | Altman et al. | 604/508 |
| 2002/0120250 A1 | * | 8/2002 | Altman | 604/508 |

* cited by examiner

Primary Examiner—Brian L. Casler
Assistant Examiner—Jeremy Thissell
(74) Attorney, Agent, or Firm—Watts Hoffman Co., L.P.A.

(57) ABSTRACT

A surgical device for injecting a chemical agent within a subject for use in endoscopic injection therapies is disclosed. The device includes a support body, a motion transmitting unit, an agent delivery system and a guide housing. The motion transmitting unit is movable relative to the support body. The agent delivery system includes a needle for extending into a subject and structure defining a conduit between the support body and the needle. The guide housing has a flexible elongated body, an internal elongated passage and friction reducing material lining the passage. At least a portion of the motion transmitting unit adjacent the needle is slideably housed within the guide housing. The device offers a surgeon improved ease of needle extension and retraction when the distal end of the endoscope is bent at acute angles.

14 Claims, 4 Drawing Sheets

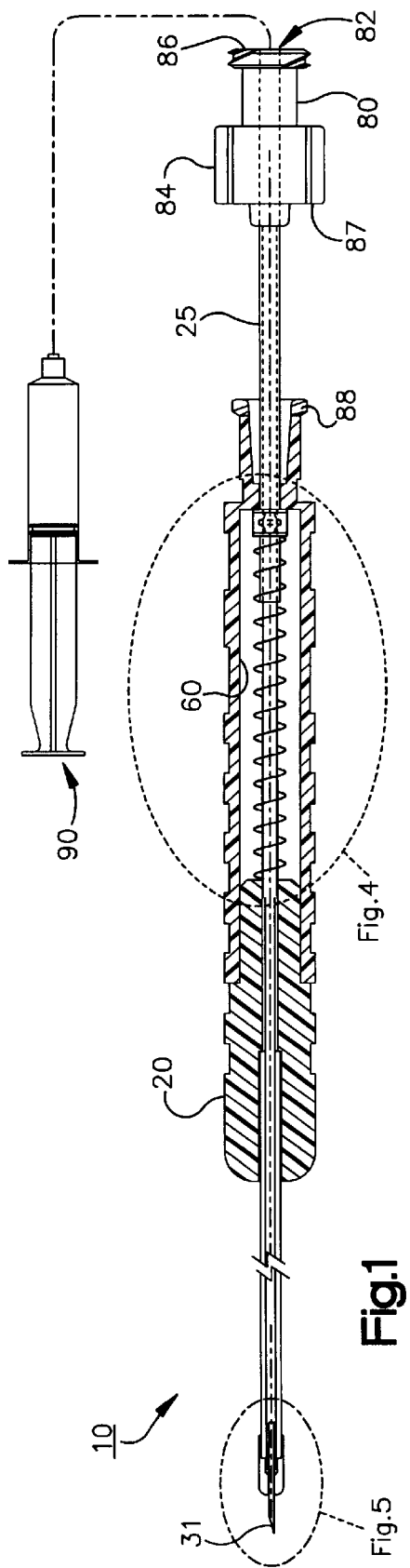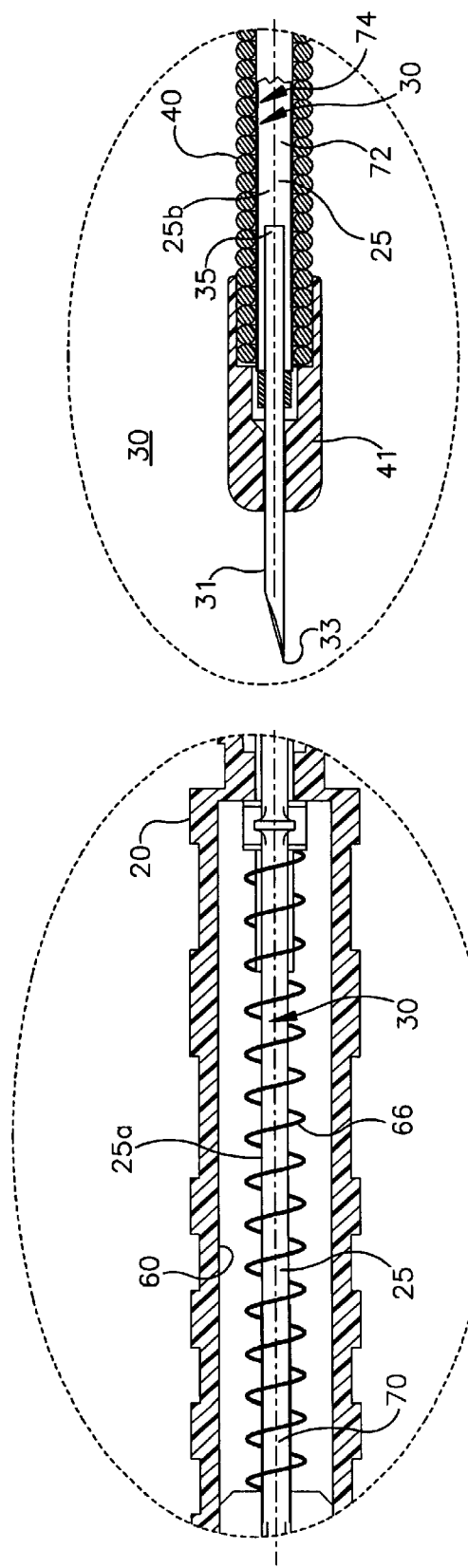

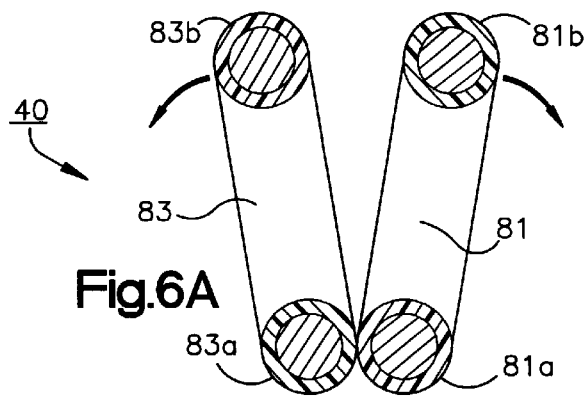
Fig.6A
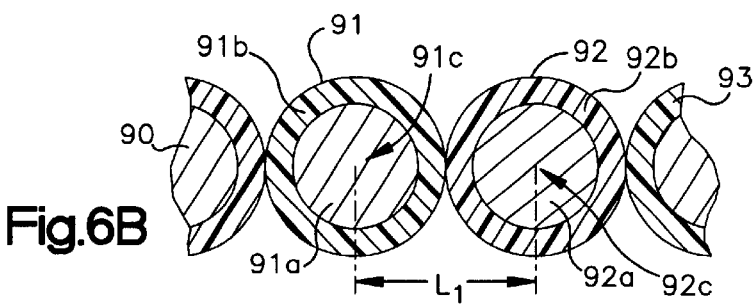
Fig.6B
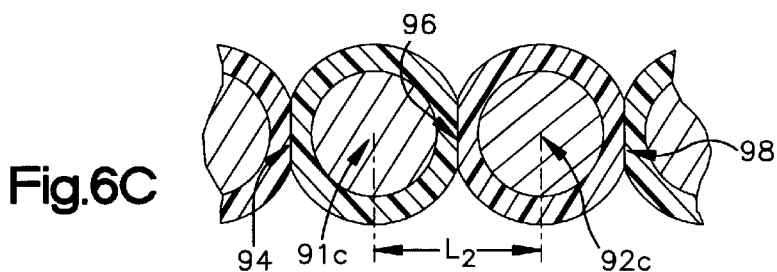
Fig.6C
| | SCOPE STYLE A | | | SCOPE STYLE B | | |
| | ELEVATOR ARM POSITION | | | ELEVATOR ARM POSITION | | |
| OEM NEEDLE MODEL | OPEN | HALF | FULL | OPEN | HALF | FULL |
|---|---|---|---|---|---|---|
| 1 | YES | NO | NO | NO | NO | NO |
| 2 | YES | YES | NO | NO | NO | NO |
| 3 | YES | YES | NO | NO | NO | NO |
| 4 | YES | YES | NO | NO | NO | NO |
| 5 | YES | YES | YES | YES | YES | NO |
NOTE: Yes or No entry indicative of whether needle passed through scope to distal end
Fig.7

|  | SCOPE STYLE A | | | SCOPE STYLE B | | |
|---|---|---|---|---|---|---|
|  | ELEVATOR ARM POSITION | | | ELEVATOR ARM POSITION | | |
| OEM NEEDLE MODEL | OPEN | HALF | FULL | OPEN | HALF | FULL |
| 1 | YES,z | YES,x,z | NO | YES,x | NO,x | NO,x |
| 2 | YES,z | YES,z | NO | YES,x,z | NO,x | NO,x |
| 3 | YES,z | YES,z | NO | YES,x,z | NO,x | NO,x |
| 4 | YES,z | YES,z | NO | YES,x,z | NO,x | NO,x |
| 5 | YES,z | YES,z | YES,z | YES,z | YES,z | YES,x,z |

NOTE: Yes or No entry indicative of whether needle deployed out of the distal end of the scope
x—indicates that deployment occurred only after arm and/or scope position was relaxed
z—indicates flow of chemical agent out needle was confirmed

Fig.8

NEEDLE KINK ANALYSIS

| OEM NEEDLE | FORCE TO KINK(grams) | |
|---|---|---|
|  | @ 2" | @ 6" |
| 1 | 309g | 87g |
| 2 | 320g | 96g |
| 3 | 330g | 101g |
| 4 | 300g | 83g |
| 5 | 900g | 594g |

DUODENOSCOPE NEEDLE

CROSS-REFERENCE TO RELATED APPLICATIONS

This non-provisional application claims benefit of U.S. Patent Provisional Application Serial No. 60/292,169, entitled "Duodenoscope Needle," filed on May 18, 2001.

FIELD OF THE INVENTION

The present invention relates to surgical devices and more particularly to surgical devices constructed for endoscopic injection therapy.

BACKGROUND OF THE INVENTION

Endoscopic injection therapy was first used to stop certain types of internal bleeding as early as 1939. This therapy method involves the injection of a chemical agent through a needle injector into or around a bleeding site within the human body to stop excessive bleeding. A variety of other applications for endoscopic injections have been developed, including biliary duct treatments.

Bile is a bitter yellow or greenish liquid that is secreted by the liver into the gastrointestinal tract. Bile aids in the digestion of fats and enters the stomach through the bile duct. In some cases, the bile duct can become blocked. This condition causes jaundice and can lead to further complications. Conventional solutions to this problem have included using an endoscopic surgical tool to cut open a portion of the bile valve. Although this procedure typically is successful in opening the valve sufficiently for bile flow, excessive bleeding is a common and dangerous complication with this and other similar procedures.

Procedures for treating the bile duct blockage, as well as treating subsequent bleeding caused by the procedures, have been limited by the relative inaccessibility of the valve. In a typical endoscopic procedure to stop excessive bleeding, a surgeon uses an endoscope to visualize the bleeding site, and then passes the needle through the instrument channel until it reaches the distal end of the scope. The surgeon then extends the needle into a subject to deliver a chemical agent. In a biliary injection procedure, the target area is the bile duct and areas adjacent the cut location.

The outlet port of the bile duct is located at an undesirable angle, making access difficult by conventional endoscopic injection therapy techniques. Although surgeons in most cases can maneuver a scope into a desired position, extending the needle in order to inject the chemical agent is made prohibitively difficult by the bile duct location.

When the distal end of a conventional endoscope is bent acutely in order to access the bile duct, the kinetic friction on internally moveable parts increases. Using conventional injection therapy devices within a scope, surgeons experience difficulty in extending needles prior to injecting the chemical agent. Even if a surgeon can successfully extend the needle, there is an equal difficulty in retracting the needle after injection of the chemical agent. In a severe case, the surgeon may be forced to withdrawn the endoscope with the needle still partially extended out of the endoscope. This undesirable condition can cause injure to the patient.

Consequently, a cut made in the bile duct is typically clotted with conventional media to stop bleeding. This technique is not without failure. About half of the deaths due to post-surgical complications of bile duct treatments are caused by excessive bleeding.

The present invention provides a new and improved therapeutic injection device for use in endoscopes that is particularly beneficial in biliary endoscopes for hemorrhage control. The device features very low internal kinetic friction enabling ease of needle extension. Moreover, the design allows extreme flexibility and low friction needle extension and retraction at acute angles near the tip of the device. The device also features precise and repeatable operational features in regard to the length of the device. The invention can be modified for use with a variety of endoscopes, including a duodenoscope having side viewing optics and a side exiting instrument channel.

SUMMARY OF THE INVENTION

In an illustrated embodiment of the invention a surgical device for use in endoscopic injection therapy is provided including a support body, a motion transmitting unit, an agent delivery system and a guide housing.

The motion transmitting unit includes a first end portion proximal to the support body and a second end portion remote from the support body. The motion transmitting unit is movable relative to the support body.

The agent delivery system includes a needle and structure defining a conduit. The needle is disposed remote from the support body. The needle has a hollow elongated body, a first end for extending into a subject, and a second end fixed to the motion transmitting unit. The conduit extends between the support body and the needle.

The guide housing for guiding the needle has a flexible elongated body and includes an end portion proximal to the needle, an internal elongated passage and friction reducing material. At least a portion of the motion transmitting unit adjacent the needle is slideably housed within the guide housing.

The motion transmitting unit may include an elongated flexible tube forming the conduit. The motion transmitting unit may include a first member constructed from hypodermic needle stock and a second member constructed from flexible tubing.

The guide housing may be constructed from flexible tubing defining an internal diameter lined with a friction reducing material. The guide housing may be constructed from a helically wound wire spring forming an internal elongated passage, wherein at least a part of the wire is coated with a friction reducing material. The friction reducing material may be Polytetraflouorethylene.

The agent delivery system may include a return mechanism having a spring for returning the needle to a non-extended position within the guide housing.

The guide housing may be conditioned prior to use, whereby a length of the guide housing remains essentially fixed during routine use such that the needle is disposed within the guide housing when in a non-extended position.

A method of making a surgical device including the step of conditioning the guide housing prior to use is also disclosed. The conditioning may include repetitively coiling the guide housing in an alternating pattern until the initial length shortens to essentially the desired length. Alternatively, the conditioning may include axially compressing the guide housing under force until the initial length shortens to essentially the desired length.

The present invention offers advantages over devices available in the prior art. The device offers low internal kinetic friction allowing ease of needle extension and retraction while the distal end of the scope is bent at acute angles. The device further offers the surgeon increased needle control and range of movement outside of the endoscope.

The increased range of needle movement increases available target areas within the subject, while at the same time, decreasing procedural performance time. In addition, the device also features precise, repeatable and safe operational features in regard to the length of the device.

Further features and advantages of the invention will become apparent from the following detailed description of an illustrated embodiment made with reference to the accompanying drawings.

BRIEF DESCRIPTION OF THE DRAWINGS

FIG. 1 is an elevational view, shown partly in cross section, of a surgical device constructed according to the present invention;

FIG. 4 is an enlarged fragmentary view of another part of the device illustrated in FIG. 1;

FIG. 5 is an enlarged fragmentary view of yet another part of the device illustrated in FIG. 1;

FIG. 6A is an enlarged cross-sectional fragmentary view of one part of the device illustrated in FIG. 1, showing two elements within the guide housing, illustrated with a portion of the device in an acutely bent position;

FIG. 6B is an enlarged cross-sectional fragmentary view of one part of the device illustrated in FIG. 1, showing a portion of a series of adjacent elements within the guide housing;

FIG. 6C is an enlarged cross-sectional fragmentary view of one part of the device illustrated in FIG. 1, showing a portion of a series of adjacent elements within the guide housing after repeated use of the device;

FIG. 7 is a chart of experimental data observed during testing of a prototype example assembled in accordance with the present invention;

FIG. 8 is a graph of experimental data observed during additional testing of a prototype example assembled in accordance with the present invention;

FIG. 9 is a graph of experimental data measured during yet additional testing of a prototype example assembled in accordance with the present invention; and FIG. 10 is a schematic representation of the experiment conducted when collecting the data illustrated in FIG. 9.

BEST MODE CONTEMPLATED FOR CARRYING OUT THE INVENTION

Figure 2:
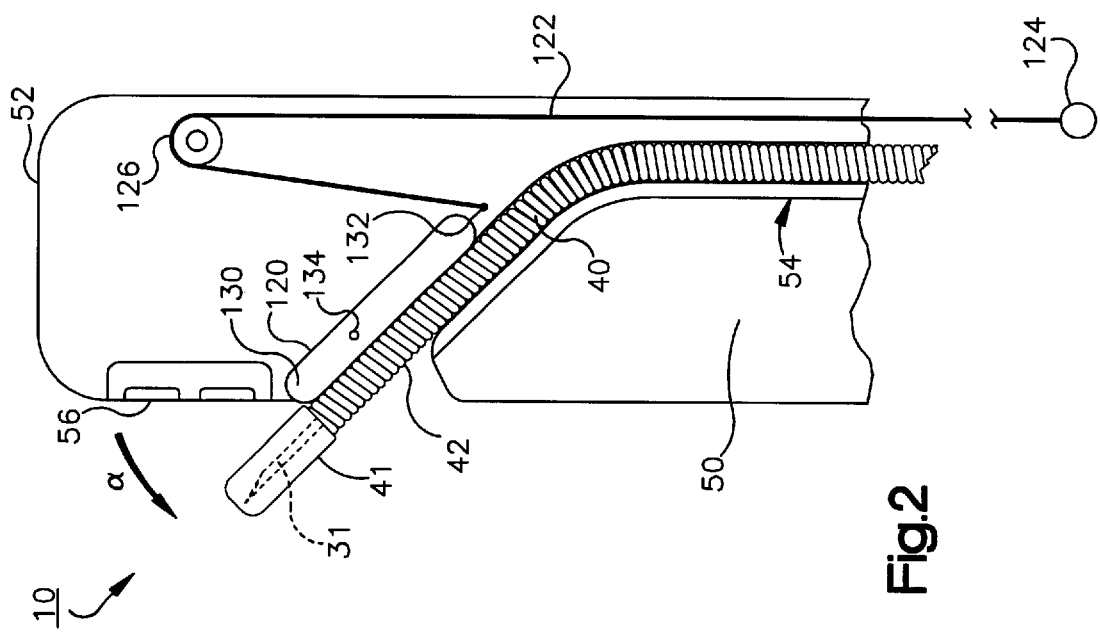
FIG. 2 is an enlarged fragmentary view of one part of the device illustrated in FIG. 1, illustrated within an endoscope with the distal end of the scope in a relaxed position.

A surgical device 10 for injecting a chemical agent into a subject for use in endoscopic injection therapies is illustrated by the drawings. Referring to FIGS. 1 and 2, the device 10 comprises a support body 20, a motion transmitting unit 25, an agent delivery system 30 and a guide housing 40.

The device 10 is so constructed and arranged that it may be inserted into a proximal end of an endoscope, or similar device. The agent delivery system 30 and guide housing 40 are further constructed and arranged so that they may be controlled by a surgeon during operation of an endoscopic device. The present invention advantageously allows the surgeon to inject a chemical agent into a human subject at a precise, desirable location. The chemical agent is injected into the subject via a needle 31 located at the distal end of the device 10. While the needle is safely recessed into the device, the surgeon can manipulate the needle into the desired position. The device 10 offers new and improved range of needle movement to increase available target areas within the subject.

Figure 3:
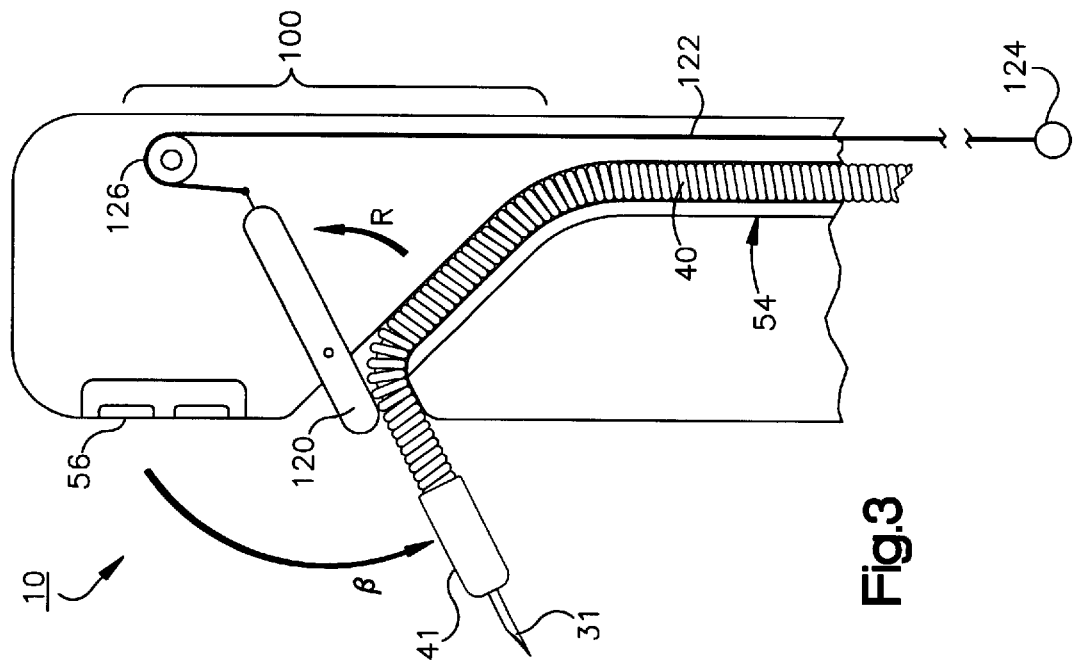
FIG. 3 is a view similar to FIG. 2, with parts illustrated in alternative positions.

The device 10 can be used with any suitable or conventional endoscopic surgical equipment. For purposes of this disclosure, the device 10 is described in the context of use with an optical endoscopic apparatus. A conventional endoscope 50 is illustrated in FIGS. 2 and 3. The endoscope is provided with an elongated body having a controllably flexible projecting end region 52. Surgical instruments, such as a device 10 constructed in accordance with the present invention, may be introduced through an instrument channel 54, which extends axially throughout the body of the scope. In addition, the scope has optical features 56 that are used by the surgeon to visualize the positioning of the needle 31. The scope may further include an arm elevator mechanism for manipulating the needle into a desired position prior to exiting the instrument passage.

When the device 10 has been inserted into the endoscope 50 and properly positioned, the surgeon grasps the body 20 for controlling the administration of the agent to the patient. As illustrated, the body 20 is an elongated piece formed from molded plastic material. The body includes an internal passage 60 through which portions of the motion transmitting unit 25 and the agent delivery system 30 traverse.

The motion transmitting unit 25 is used by the surgeon to transmit motion to the needle 31. The motion transmitting unit 25 includes a first end portion 25a proximal to the support body 20 and a second end portion 25b remote from the support body. The motion transmitting unit 25 is movable relative to the support body 20.

In the illustrated embodiment, the motion transmitting unit 25 includes a first member 70 and a second member 72. The first member 70 is rigid and is fixed to the second member 72. As illustrated, the first member 70 is constructed from conventional hypodermic needle stock and remains stiff under manually applied axial force. The second member 72 is constructed from flexible tubing having an internal passageway 74. In illustrated embodiment, the internal passageway 74 has a structure defining a conduit between the support body 20 and the needle 31.

The second member 72 bends within the endoscope internal passage 54 when manipulated by the surgeon. The second member may be formed from any suitable material stock, so that it can flex to an acute angle and still push the needle. The second member 72 has good compressive and tensile strength and is somewhat resiliently bendable and will bend appreciably without yielding and kinking.

The second member 72 is fixed to the needle 31 at a needle second end 35. The second member 72 is so constructed and arranged to transmit considerable deployment forces to the needle 31 while enabling the scope body to be freely manipulated and flexed to position the needle 31 where desired.

In the embodiment shown, the motion transmitting unit 25 includes a fitting 80 movable with respect to the support body 20 for manually transmitting motion to the needle 31. As the surgeon moves the fitting 80 in a direction of the needle 31, forces are imparted upon the first member 70. Consequently, axial forces imparted to the first member 70 are transmitted to the second member 72.

In an alternative embodiment, the entire motion transmitting unit 25 may be constructed from an elongated flexible tube.

Forces imparted on the second member 72 are transmitted to the needle 31 such that a portion of the needle is extended beyond a distal end of the device 10. Referring to FIG. 2, a needle 31 is illustrated in a recessed position. After the distal end of the device 10 is manipulated into a desired position, the needle is extended. The needle 31 is illustrated in an extended position in FIG. 3.

A agent delivery system 30 for delivering a chemical agent to a subject is disclosed. The agent delivery system 30 includes a needle 31 and system having a structure defining a conduit between the support body 20 and the needle 31.

The needle 31 is disposed remote from the support body 20. As illustrated, the needle has a hollow elongated body, a first end 33 for extending into a subject, and a second end 35. The second end 35 is fixed to the motion transmitting unit 25 by conventional means.

Referring now to FIG. 5, in the illustrated embodiment the needle 31 is a conventional hypodermic needle. The needle end 33 may be angled with respect to a needle longitudinal axis at 30° or any other suitable angle. As illustrated, the needle 31 is in communication with a conduit 74. The conduit is defined by the internal passageway of the second member 72. The conduit 74 is disposed between the support body 20 and the needle 31, and provides a passageway for the chemical agent.

As illustrated, the agent delivery system 30 includes a syringe 90. The syringe 90 may be disposed adjacent to the support body 20 by a surgeon for delivering a chemical agent to the needle 31 located at a distal end of the device 10.

The device 10 also includes a guide housing 40 for guiding the needle 31. The guide housing has a flexible elongated body and includes an end portion proximal to the needle and an internal elongated passage lined with a friction reducing material. At least a portion of the motion transmitting unit 25 adjacent the needle is slideably housed within the guide housing 40. The guide housing end portion may include a cap 41 at the distal end of the housing 40. As illustrated in FIG. 5, the cap 41 fixedly joins the needle 31, guide housing 40 and the second member 72.

In the illustrated embodiment, the guide housing is a flexible sheath 40. The sheath is formed by a helically wound wire spring forming an internal elongated passage. The wire is coated with a friction reducing material. This low friction material allows a surgeon to easily pass the needle through the internal passage and also then extend the needle 31 when the distal end of the endoscope is bent at an acute angle, as illustrated in FIG. 3.

The friction reducing material may be Polytetraflourethylene, known as PTFE, or any other suitable material. In an alternative embodiment, the same or similar material be used only on the inside of the guide housing 40.

As discussed, the second member 72 and sheath are flexible and can be bent by the user. When the sheath 40 is bent in one direction, portions of adjacent spring elements on the inside of the bend press together, while portions of adjacent spring elements on the outside of the bend separate. Referring to FIG. 6A, two winding elements 81, 83 of the sheath 40 are shown. FIG. 6A is an enlarged cross-sectional fragmentary view of one part of the device 10 illustrated in FIG. 1, showing a portion of the device in an acutely bent position. As illustrated, two end portions 81a, 83a of two adjacent elements 80, 81 on the inside of the bend press together, while two opposing end portions 81b, 83b of adjacent spring elements on the outside of the bend separate.

The operation of the device 10 in concert with the endoscope 50 will now be discussed in greater detail. As illustrated, endoscope 50 in constructed and arranged to allow for manipulation of the device 10. Specifically, the endoscope 50 includes an arm manipulation control system 100. The arm manipulation control system 100 comprises an arm 120, a cable 122, a needle manipulator unit 124 and a pulley 126. Referring to FIG. 2, the arm manipulation system 100 is illustrated in a relaxed position. In the relaxed position, an acute angle α is formed between a longitudinal axis of the device 10 and an injection needle 31.

Referring now to FIG. 3, the distal end of sheath 40, and the second member 72 housed within the sheath, are illustrated in an articulated condition. An obtuse angle β is formed between a longitudinal axis of the device and the injection needle 31. These two angles α, β generally represent the range of needle movement available to a surgeon operating the device 10.

The present invention offers a surgeon increased control of the needle 31 outside of the endoscope. In the illustrated embodiment, the surgeon may manipulate the needle through a range of angles. Referring to FIGS. 2 and 3, the range of movement in the illustrated embodiment is defined by a range from a relaxed position to an articulated position, defined by angles α to β respectively. As illustrated, angle α is about 45° and angle β is about 120°. It should be apparent to those skilled in the art that, in light of this disclosure, other angles may be used in the practice of this invention.

The arm 120 includes a first end 130, a second end 132, and a pivot point 134. The arm 120 as illustrated may be an elongated member fixed within the interior of the distal end of the scope. The first end 130 may be adjacent a structure in communication with an injection needle 31. A cable 122 is fixed to the second end 132.

As seen in FIGS. 2 and 3, the arm 120 is rotationally mounted at a pivot point 134. Any suitable or conventional mounting method may be used. The arm is supported at the pivot point 134 so that the cable 122 can effectuate movement of the arm. As illustrated, the arm 120 is an elevator arm that can be used to advantageously manipulate the position of the needle 31 with respect to targeted areas in the surgical field.

The cable 122 extends from the second end 132 of the arm to a needle manipulator unit 124. As illustrated, the cable 122 is a thin, flexible wire. The cable 122 may extend within the longitudinal passage 54. The cable 122 may be constrained within the passage to allow translational longitudinal motion.

The needle manipulator unit 124 is operated by the surgeon to position the injection needle 31 in a desired location within the subject As illustrated in FIG. 2, the surgeon may rely upon side viewing optics 56 to view the surgical field. In the case of a biliary duct treatment, after a cut has been made in the duct, the surgeon continues to view the duct area to identify points of relevant bleeding. After target areas are identified, the surgeon may operate the needle manipulator unit 124 in order to move the tip of the injection needle 31 to a desired position.

As illustrated in FIG. 2, the needle actuator unit 124 may be a ring or similar manual device operable by the surgeon. As the ring 124 is moved in a direction opposite the distal end of the scope, the cable 122 acts to move the second end 132 of the arm toward the pulley 126. The arm rotates in a direction illustrated by the arrow R in FIG. 3. In concert, the first end 130 rotates in the same direction R. The first end 130 contacts a distal end portion 42 of the sheath 40 near the needle 31 and proportionally rotates the needle 31 to a desired position.

The pulley 126 is included for supporting the cable 122 between the arm and the needle manipulator unit 24. The pulley is mounted within the distal end 52 of the scope 50. As illustrated in FIGS. 2 and 3, the pulley may be disk-shaped and include a circumferential groove for adequately containing the cable 122 during movement. Any suitable or conventional pulley may be used.

Once the needle 31 is manipulated into a desired position, the surgeon extends the needle 31 into the subject by use of the motion transmitting unit 25. In the illustrated embodiment, the surgeon may press a thumb against a handle 86 in the direction of the needle 31 while holding the support body 20 with two or more fingers. The axial movement of the handle 86 relative the body 20 forces the first end 33 of the needle 31 to embed within the subject. After sufficient manual force is applied, a mating surface 87 of the fitting engages a mating surface 88 of the support body 20. The fitting 80 is then held by the surgeon along a surface 84. As illustrated, the fitting 80 may be manually rotated so that the surface 87, 88 are removably fixed. The surgeon can now release his or her grip of the fitting 80 without the needle 31 dislodging from the subject.

After a first end 33 of the needle 31 embeds within the subject, the surgeon delivers the chemical agent by using the syringe 90. The distal end of the syringe is inserted into an opening 82 within the fitting 80. The opening 82 is in communication with the internal passageway 60 of the support body 20. The first member 70 and the second member 72 communicate to transport the agent to the needle 31.

It should be apparent to others with ordinary skill in the art in view of this disclosure, that any suitable liquid transporting apparatus may be used to pressure the agent. Further, it should be apparent to others with ordinary skill in the art in view of this disclosure, that a second dedicated passageway within the device 10 may be used to transport a chemical agent to the needle 31. This second dedicated passageway may be structurally separate from all or a portion of the motion transmitting unit 25.

After the surgeon injects the chemical agent into the subject, the device may be conveniently removed. As illustrated, a spring mechanism 66 is included and disposed internally within the body 20. The spring mechanism 66 is constructed and arranged so that it is compressed during periods of needle 31 extension. The spring may be fixed at a first end with respect to the first member 70 and at a second end with respect to the support body 20. When a surgeon the fitting 80 from the body 20 at a conclusion of the procedure, the spring 66 relaxes and the first member 70 is moved in a direction opposite the needle 31. This spring generated force acts to return the needle to a non-extended position within the distal end of the endoscope.

In the development of the present invention, a previously unknown problem was discovered. Although the device is primarily designed to be a single use device, the amount of handling of the device in the field is beyond the control of the design. Devices may be repackaged, practiced with by inexperienced users, used for demonstrations, or otherwise handled prior to use. The pressing together of adjacent spring windings during handling had an unexpected effect of shortening the length of the guide housing.

Referring to FIG. 6B, an enlarged cross-sectional fragmentary view of one part of the device is illustrated, showing a series of adjacent elements within one wall of the sheath 40. The device is illustrated prior to initial use. The fragmentary view illustrated includes four adjacent winding elements 90, 91, 92, 93. For exemplary purposes only, two elements 91, 92 will be discussed.

As illustrated, each winding element 91, 92 includes an interior portion 91a, 92a and an exterior portion 91b, 92b. The interior portion is a metallic material adapted to be wound into an elongated member 72. As discussed, the exterior portion 91b, 92b is a friction reducing coating. In the illustrated embodiment, the exterior portion 91b, 92b is PTFE.

The overall length of the sheath 40 is a function of the cumulative width of the wound elements. The width of a wound element can be equated to and measured by the distance between center points of adjacent wound elements. As illustrated in FIG. 6B, the distance $L_1$ between one element 91 and an adjacent element 92 is defined by the distance between the two element center points 91c, 92c.

During routine use of the device, the sheath 40 is commonly bent in a variety of directions. The sheath may be bent when the device is coiled after manufacturing in anticipation of packaging. Further, the second member is also bent when is use in a endoscope, as illustrated in FIG. 3.

The repeated bending of the sheath 40 is believed to shorten its application length. Referring now to FIG. 6C, an enlarged cross-sectional fragmentary view is illustrated, showing a portion of the same device shown in FIG. 6B, but after repeated use of the device. The distance between center point 91a and an adjacent center point 92a is defined by a distance $L_2$, reduced from the initial distance $L_1$. The cause of the reduction in the distance from $L_1$ to $L_2$ may be apparent from FIG. 6C. As a result of the pressing together of adjacent windings, flat sections 94, 96, 98 develop in the coating. The flat sections are areas of thinning coating and cumulative act to shorten the overall length of the sheath 40.

For exemplary purposes only, a sheath 40 having an initial length of 90 inches may be shortened up to 0.5 inch in length during use of the device. In one embodiment, a sheath that is 90 inches in length typically has about 250 winding elements. The coating of each winding may have an initial thickness from 0.002" to 0.005". The reduction of thickness may be as much as 0.001" in thickness, or 0.002" per winding when measured across the diameter of a wire. In other experiments, as much as 0.75 inches in length has been lost.

Shortening of the sheath 40 a length of even 0.5 inches is significant. In some cases, the sheath may shorten undesirably so that the needle 31 no longer recesses when at rest in an unextended position. This condition makes the device 10 dangerous for use. The exposed needle may inadvertently damage the endoscope, or in severe cases, may injure the user or the patient.

In the practice of the present invention, it is important to prevent a condition where the needle does not recess into the device. Although not wanting to be bound by theory, it is believed that after coiling the device between 10 to 15 times, the flat sections in the coating remain relatively permanent and no longer thin out. Consequently, the overall length of the sheath 40 becomes fixed.

The present invention includes a method of providing a surgical device for injecting a chemical agent within a subject for use in endoscopic injection therapies. In this method, the sheath is conditioned prior to use.

The method begins with fabricating a guide housing. The housing in constructed from a helically wound wire spring coated with a low friction material to form an internal passageway. A desired length of the sheath must be determined. Next, an initial length of the sheath is chosen. This initial length is the sum of the desired length and the anticipated shortening of the sheath as a result of thinning coating. As discussed, the loss in length can be 0.5 to 0.75 inches. It should be apparent to others with ordinary skill in the art that other anticipated shortening lengths may be used in the practice of this invention. The lengths will vary depending on the coating used, the force applied during bending, as well as other factors.

After the device in accordance with the present invention is assembled, the sheath is conditioned prior to use of the device. In one technique, the device is repetitively bent in an alternating arcuate coiled pattern. In other words, the sheath is coiled in a tight circle, unwound, and then coiled in the opposite direction. This technique shortens the sheath initial length to essentially the desired length. In an alternative technique, the sheath is compressed by an axial force. It should be apparent to others with ordinary skill in the art that other conditioning techniques may be used in the practice of this invention.

Experimental Data

Experimental results of the present invention evaluated against known devices are shown in summarized form in FIGS. 7, 8 and 9. Four commercially available devices were selected as test samples for the experiments. The four devices were evaluated against a device assembled in accordance with the present invention. In FIGS. 7–9, the known devices are identified by model numbers 1–4. The device assembled in accordance with the present invention is identified as model number 5. The known devices were manufactured by four different original equipment manufacturers. Each known device was tested without modification. The experiments consistently achieved repeatable results.

Referring now to FIG. 7, a chart is provided that summarizes a test of needle passage. In this test, the five models were evaluated in use within two different scope styles. Scope style A represents a commercially available scope positioned with a straight distal end. Scope style B is the same scope, but positioned with the distal end at a 90° bend. For each scope style, three different arm positions were utilized; open, half and full. The open arm position is approximately as shown in FIG. 2, while the closed arm position is approximately as shown in FIG. 3. The half arm position is approximately between the open and full, or in other words, at an angle about half way between α and β. The two scope styles and three arm positions combine to create six different testing configurations.

In the needle passage test summarized in FIG. 7, each device was tried in all six testing configurations. The tester simply recorded whether or not the needle was able to pass to the distal end of the scope. It can be seen from the results that model number 5, the device assembled in accordance with the present invention, was the only device in which the needle passed in all six configurations.

Referring now to FIG. 8, a chart is provided that summarizes a test of needle deployment. In this test, the same five models were evaluated in the same two scope styles. As in the test summarized in FIG. 7, six testing configurations were utilized.

In the needle deployment test summarized in FIG. 8, each device was again evaluated in all six testing configuration. The tester recorded whether or not the needle was able to deploy out of the distal end of the scope. If a needle could not deploy, the tester relaxed the arm and/or scope position, and tried again. In other words, the angle of the bend was decreased with respect to a longitudinal axis. As indicated by footnote X in FIG. 8, certain needles that would not initially deploy, did deploy in a relaxed position.

Next, the tester attempted to flow a chemical agent out of the distal end of the needle. The observations of the tester are summarized in FIG. 8. It can be seen from the results that model number 5, the device assembled in accordance with the present invention, was the only device in which the needle passed, and agent flow was confirmed, in all six configurations.

Referring now to FIG. 9, a chart is provided that summarizes a test of needle kink. A depiction of the experimental configuration used is illustrated in FIG. 10. In this test, the same five models were evaluated. The sheath 40 of a device was held by a rod holder 100 and a collett holder 104.

A force was applied to a length $L_3$ of the exposed sheath 40 section of the device. The force was applied until kinking occurred A 2 inch and a 6 inch section of each device were tested. The force applied was measured by conventional equipment 102 known to those skilled in the art. The tester recorded the force in grams required to kink a portion of the device.

The recordings of the tester are summarized in FIG. 9. It can be seen from the results that model number 5, the device assembled in accordance with the present invention, had the highest resistance to kinking in both the 2 inch and the 6 inch test.

It can be seen from FIGS. 7, 8 and 9, a device assembled in accordance with the present invention, consistently and repeatedly out performed known devices in stock condition.

While a single embodiment of the invention has been illustrated and described in considerable detail, the present invention is not to be considered limited to the precise construction disclosed. Various adaptations, modifications and uses of the invention may occur to those skilled in the arts to which the invention relates. It is the intention to cover all such adaptations, modifications and uses falling within the scope or spirit of the annexed claims.

Having described my invention We claim:

1. A surgical device for injecting a chemical agent within a subject for use in endoscopic injection therapies, the device comprising:
   a. a support body;
   b. a motion transmitting unit comprising a first end portion proximal to said support body and a second end portion remote from said support body, wherein said motion transmitting unit is movable relative to said support body;
   c. an agent delivery system comprising:
      i. a needle remote from said support body having a hollow elongated body, a first end for extending into a subject, and a second end fixed to said motion transmitting unit second end portion; and
      ii. structure defining a conduit between said support body and said needle; and
   d. a guide housing for guiding said needle, said housing comprising a flexible elongated body, an end portion proximal to said needle, an internal elongated passage and friction reducing material lining said passage, wherein a part of said motion transmitting unit adjacent said needle is slideably housed within said guide housing;
   e. wherein said guide housing is constructed from a wire coated with a friction reducing material, said coated wire being helically wound to form said internal elongated passage.

2. The device claimed in claim 1 wherein said motion transmitting unit comprises an elongated flexible tube forming said conduit.

3. The device claimed in claim 1 wherein said motion transmitting unit comprises a fitting movable with respect to said body for manually transmitting motion to said needle.

4. The device claimed in claim 1 wherein said motion transmitting unit comprises a first member constructed from hypodermic needle stock and a second member constructed from flexible tubing.

5. The device claimed in claim 1 wherein said agent delivery system comprises a syringe disposed adjacent to said support body for delivering a chemical agent to said needle located at a distal end of the device.

6. The device in claim 1 wherein said agent delivery system comprises a return mechanism, said mechanism comprising a spring for returning said needle to a non-extended position.

7. The device claimed in claim 1 wherein said friction reducing material is Polytetraflourethylene.

8. The device claimed in claim 1 wherein said guide housing is conditioned prior to use, whereby a length of said guide housing remains essentially fixed during routine use.

9. The device claimed in claim 1 wherein said support body is a molded plastic structure defining an internal passageway extending through said body and communicating with said conduit.

10. A surgical device for injecting a chemical agent within a subject for use in endoscopic injection therapies, the device comprising:
   a. a support body defining an internal passageway extending through said body;
   b. a motion transmitting unit comprising a first member proximal to said support body and a second member, said unit moveable with respect to said body;
   c. an agent delivery system comprising:
      i. a needle remote from said support body having a hollow elongated body, a first end for extending into a subject, and a second end fixed to said motion transmitting unit second member; and
      ii. structure defining a conduit between said support body and said needle; and
   d. a guide housing for guiding said needle, said housing comprising a flexible elongated body, said body comprising an end portion proximal to said needle, an internal elongated passage and friction reducing material lining said passage, wherein at least a portion of said motion transmitting unit second member adjacent said needle is flexible and slideably housed within said guide housing;
   e. wherein said guide housing is constructed from a wire coated with a friction reducing material, said coated wire being helically wound to form said internal elongated passage.

11. The device claimed in claim 10 wherein said first member is constructed from hypodermic needle stock and said second member is constructed from flexible tubing.

12. The device in claim 10 wherein said agent delivery system comprises a return mechanism, said mechanism comprising a spring for returning said needle to a non-extended position within said guide housing.

13. The device claimed in claim 10 wherein said friction reducing material is Polytetraflourethylene.

14. The device claimed in claim 10 wherein said guide housing is conditioned prior to use, whereby a length of said guide housing remains essentially fixed during routine use such that said needle is disposed within said guide housing when in a non-extended position.

* * * * *